US009257029B1

(12) United States Patent
Hendrick, III et al.

(10) Patent No.: US 9,257,029 B1
(45) Date of Patent: Feb. 9, 2016

(54) SYSTEM AND METHOD OF REMOTE MONITORING AND DIAGNOSTICS FOR HEALTH CONDITIONS AND EMERGENCY INTERVENTIONS

(71) Applicants: James Robert Hendrick, III, Nashville, TN (US); Jonathan Eddy Barnes, Nashville, TN (US); Andrew Thomas Johnson, Franklin, TN (US); James E. Anderson, III, Nashville, TN (US)

(72) Inventors: James Robert Hendrick, III, Nashville, TN (US); Jonathan Eddy Barnes, Nashville, TN (US); Andrew Thomas Johnson, Franklin, TN (US); James E. Anderson, III, Nashville, TN (US)

( * ) Notice: Subject to any disclaimer, the term of this patent is extended or adjusted under 35 U.S.C. 154(b) by 58 days.

(21) Appl. No.: 14/013,114

(22) Filed: Aug. 29, 2013

Related U.S. Application Data

(60) Provisional application No. 61/694,532, filed on Aug. 29, 2012.

(51) Int. Cl.
*G08B 23/00* (2006.01)
*G08B 21/04* (2006.01)

(52) U.S. Cl.
CPC .................... *G08B 21/0407* (2013.01)

(58) Field of Classification Search
CPC ........... G08B 21/0423; G08B 21/0446; G08B 21/0453; G06F 19/3418; G06F 19/322; A61B 5/0002; A61B 5/002; A61B 5/0022; A61B 5/1117
USPC ...................... 340/573.1, 539.11, 539.12, 3.1; 600/300, 301
See application file for complete search history.

(56) References Cited

U.S. PATENT DOCUMENTS

| | | | |
|---|---|---|---|
| 5,544,649 A | 8/1996 | David et al. | |
| 6,611,206 B2 | 8/2003 | Eshelman et al. | |
| 7,034,691 B1 * | 4/2006 | Rapaport et al. | 340/573.1 |
| 7,130,383 B2 * | 10/2006 | Naidoo et al. | 379/37 |
| 7,733,224 B2 | 6/2010 | Tran | |
| 7,917,376 B2 | 3/2011 | Bellin et al. | |
| 7,978,062 B2 * | 7/2011 | LaLonde et al. | 340/539.11 |
| 8,647,268 B2 * | 2/2014 | Tran | 600/301 |

(Continued)

FOREIGN PATENT DOCUMENTS

WO 2007079154 12/2007

OTHER PUBLICATIONS

Druker, David: Innovation Center, California, Druker Center of Health Systems Innovation, "Announcing the Winners of the link-Ages Kickoff Weekend Developer" (Apr. 24, 2012).

*Primary Examiner* — Eric Blount
(74) *Attorney, Agent, or Firm* — Patterson Intellectual Property Law, P.C.; Lucian Wayne Beavers; Gary L. Montle

(57) ABSTRACT

An automated healthcare intervention system includes biometric and activity sensors in a residential area. A server stores base data for an associated healthcare subject in a data storage network, and leverages the base data to infer temporal relationships with respect to potential conditions for the subject. The server determines that an event requiring intervention has occurred by comparing combinations of base data and inferred temporal relationships with associated time ranges and threshold values, and delivers an intervention prompt to an associated healthcare provider. Post-event monitoring allows for predictive analysis with respect to future occurrences of a similar event, and further enables determination of a severity of the event, for example a fall. Defined sleeping areas or food storage areas may be monitored over time and with respect to defined patterns and healthcare conditions of the subject to identify sleeping or eating disorders.

19 Claims, 11 Drawing Sheets

(56) References Cited

U.S. PATENT DOCUMENTS

| | | | |
|---|---|---|---|
| 8,942,817 B2* | 1/2015 | Hyde et al. | 607/60 |
| 8,961,414 B2* | 2/2015 | Teller et al. | 600/301 |
| 2003/0181790 A1 | 9/2003 | David et al. | |
| 2003/0208109 A1 | 11/2003 | David et al. | |
| 2007/0152837 A1* | 7/2007 | Bischoff et al. | 340/573.1 |
| 2008/0001735 A1* | 1/2008 | Tran | 340/539.22 |
| 2008/0167535 A1* | 7/2008 | Stivoric et al. | 600/301 |
| 2010/0145164 A1 | 6/2010 | Howell | |
| 2013/0150686 A1* | 6/2013 | Fronterhouse et al. | 600/323 |

* cited by examiner

FIG. 3

SYSTEM AND METHOD OF REMOTE MONITORING AND DIAGNOSTICS FOR HEALTH CONDITIONS AND EMERGENCY INTERVENTIONS

BACKGROUND OF THE INVENTION

The present invention pertains to systems, methods and readable medium providing remote monitoring services for people at risk for health conditions and communication of potential emergent health situations to third parties.

Health conditions including the onset of old age often present situations in which patients are unable to provide for their own care. These patients are considered "at risk" and as such often require supervision (monitoring) on a consistent and/or ongoing basis. At risk persons may be prone to certain emergent events such as stroke, coronary events, falls, etc. They may also be suffering from decreased mental capacity, frailty and/or the effects of aging.

The benefits of a patient being able to recuperate and/or age in familiar surroundings are well-documented. That is just one of the many advantages of remaining in the home including the financial advantage when compared to cost of an assisted living facility or other medical facility.

Today, remote monitoring systems are widely used in the home security industry as well as in patient monitoring applications. Remote Monitoring Systems typically consists of sensors and a central control device (i.e. PCB). When a sensor is tripped, a communication is initiated (i.e. via phone line, cell, etc.) to a central monitoring source (i.e. call center) that can provided automated response and/or live response to assess and address an emergent situation. Sensors for home security systems typically include motion detectors, door contacts, smoke detectors, flood detectors and/or video cameras. Patient monitoring systems may also include bed/chair pressure pads as well as personal emergency response systems (i.e. panic buttons).

To better control the cost of healthcare services, many providers and insurers are using electronic and automated technologies to minimize the amount of human resources required to deliver services. This is true of the remote monitoring services of at risk patients as well. Manual monitoring by human supervision is costly, subject to human error and often inconsistent across multiple caregivers.

Yet according to the AARP, 89% of seniors prefer to remain living independently in their homes as they age. As is widely noted, the baby boomers are entering into the ranks of senior citizens, and the need for solutions that will allow them to do so and remain in their homes safely is clear.

For patients seeking to remain living independently, self-monitoring is one option. Self-monitoring solutions require a patient to request assistance with a panic button or comparable one-touch emergency response technology. These systems have proven to be less than sufficient for various reasons. Non-compliance (i.e. failure to wear the device) is a primary cause. In addition, studies have shown that as much as 50% of patients who experience a fall or other medical condition while wearing the device are disoriented or otherwise incapacitated to the point that they do not utilize the device.

Another option to remain living independently is to utilize layperson and/or professional caregivers. If the patient has family members and/or friends they may act in the role of informal caregiver and monitor the patient. However, they are often unable to cover the full 24-hour period, and/or are obligated otherwise (i.e. a career commitment) and/or are not familiar with the needs of the task and/or otherwise unable to fulfill the monitoring duties. There also exist questions regarding continuity and consistency of the monitoring.

Professional caregivers may also provide care in conjunction with or independent of informal caregivers. Professional caregivers, both skilled (i.e. nurses) and non-skilled (household taskmasters), come at an expense. These services may be provided on a less than 24 hour basis. However, sufficient coverage by caregivers may not be possible either due to financial constraints and/or the preference of the patient and/or caregivers.

Additionally, the caregiver or a group of caregivers may not be able to provide a complete, accurate and consistent monitoring.

Remote collection of biometric data to assess and/or monitor the condition of at risk patient has emerged as a widely accepted alternative to keeping a patient in a hospital-stay observation.

Many early versions of remote biometric monitoring utilized data collection devices at the source that would record over a period of time and then be returned in order for the data to be extracted and analyzed.

Those systems evolved with the proliferation of communication technologies (i.e. internet, cellular, 3G, etc.) that no longer required physical access to the recording device in order to access the data.

Economies of scale and technology allowed more cost effective monitoring devices to be developed. The proliferation of internet, cellular and other digital communications continues to reduce the cost of monitoring at risk patients long term or even in perpetuity. These systems also evolved to more offer real-time data analysis and event monitoring.

Many biometric devices as are currently known in the art (e.g. weight scales, glucose meters, pulse/oximeters and blood pressure) are effective when in use but are unable to capture activities of daily living which can be indicative of an emergent condition.

Similar to biometric monitoring, remote security systems as are currently known in the art (motion detectors, door contacts, pressure pads, flood detectors, etc.) have found comparable economies of scale and have benefited from the proliferation of communications options.

Remote monitoring systems have the ability to capture lifestyle activity, and both systems are focused on protecting the well-being of the individual utilizing them. When combined, these systems are better able to determine a cause and effect relationship between lifestyle and a health-threatening event, and provide more comprehensive monitoring for the patient.

Thus, there is a need for a product that combines biometric data reporting and lifestyle data in order to provide a more complete approach to remote patient monitoring.

More particularly, there is a need for a system that allows a patient to continue to live independently while providing comprehensive (24 hour) monitoring, alerting caregivers to emergent situations, and providing analytical reporting to enable quality care of at risk patients.

This need is particularly relevant in the context of falls, as alluded to previously. According to the CDC in 2010, over 50% of falls among seniors were never reported to a health professional. This is attributed to several different factors including but not limited to the embarrassment of the senior, the senior being unaware of the implications and importance of reporting the fall, and concern that knowledge of the fall may lead relatives and/or health professionals to change the seniors living conditions.

However, previous falls are a strong indicator of the potential for future falls. In fact, fall scores (the number of previously recorded falls) are used as best practice as a quantifiable method for determining certificate of need for senior care.

Based on 2010 U.S. Census data, 1.5% of seniors (age 65 and older) will have a fall that requires hospitalization. With over 40 million seniors in 2010, the average cost of a fall requiring hospitalization was $17,500, making this an estimated $10 billion annual healthcare expenditure. The trend of an increasingly larger population over the age of 65 and rising costs in healthcare has led healthcare providers and health plans to seek technology solutions to help maintain a healthy population and control healthcare costs.

Therefore, there is further a need for a low cost and non-obtrusive technology solution for predicting falls before they occur to keep seniors healthier, allow those seniors to remain in their homes longer, and help both seniors and health plans avoid downstream costs.

BRIEF SUMMARY OF THE INVENTION

One embodiment of a system for diagnosing and prompting healthcare interventions according to the present disclosure includes a set of biometric sensors and a set of living activity sensors disposed in a defined residential area for a healthcare subject. A host server receives output signals from the sensors and stores base data as time-specific biometric and activity data points for the subject in a data storage network. An inference program engine determines derivative data as one or more inferred temporal relationships with respect to the base data, wherein additional program engines determine the occurrence of an event requiring intervention by comparing one or more combinations of base data and derivative data with associated temporal ranges and/or threshold values. Upon determining such an event, the host server delivers an intervention prompt to a healthcare provider associated with the subject.

In another embodiment, the system identifies one or more periods of inactivity in at least a portion of the defined area from the derivative data, wherein the one or more periods of inactivity have at least a threshold duration. An event requiring intervention is determined wherein one or more of the identified periods of inactivity correspond to a period of expected activity.

In another embodiment, the system identifies a duration or frequency of activity with respect to at least a portion of the defined area from the derivative data. An event requiring intervention is determined wherein the respective duration or frequency of activity exceeds a threshold value for the subject.

In one aspect of various embodiments of a system and associated methods of the present disclosure, a user interface enables users to provide input relevant to a healthcare profile for the subject, wherein an initial set of intervention criteria is defined based in part on the healthcare profile.

In another aspect of a system and method of the present disclosure, intervention criteria such as threshold values or time durations associated with the subject are dynamically adjusted over time based on determined events and patterns in the stored base data and determined derivative data.

In another aspect of a system and method as disclosed herein, data comprising determined events, associated base data and associated derivative data is aggregated in a data storage network, and the aggregated data is implemented as predictive indicators of future such events. Intervention criteria such as threshold values or time durations associated with the subject may be dynamically adjusted over time based on the aggregated data as predictive indicators.

In another aspect of a system and method as disclosed herein, post-event monitoring of one or more predetermined base data and derivative data combinations may be used and analyzed to determine a severity of a respective event.

BRIEF DESCRIPTION OF THE SEVERAL VIEWS OF THE DRAWINGS

FIG. 3 is an image representing a screen shot from an exemplary user interface generated by a system according to the present invention.

DETAILED DESCRIPTION OF THE INVENTION

Figure 1:
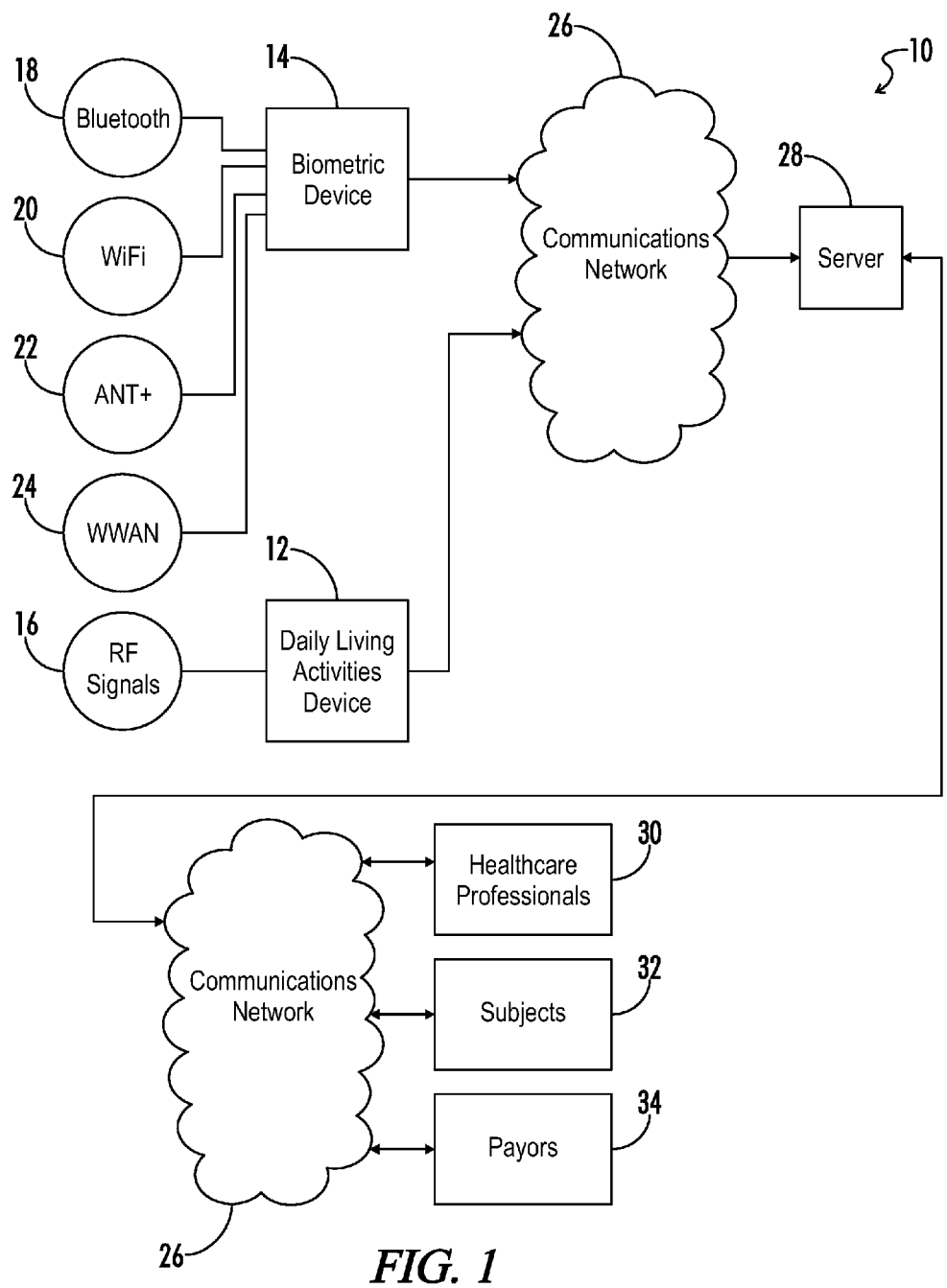
FIG. 1 is a block diagram representing an embodiment of a host system in accordance with the present invention.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Referring generally to FIGS. 1-8, exemplary embodiments of devices, systems and methods for automatically assessing healthcare needs, facilitating healthcare resource allocation and generating a hosted user interface according to the present disclosure may now be described. Where the various figures may describe embodiments sharing various common elements and features with other embodiments, similar elements and features are given the same reference numerals and redundant description thereof may be omitted below.

Figure 2:
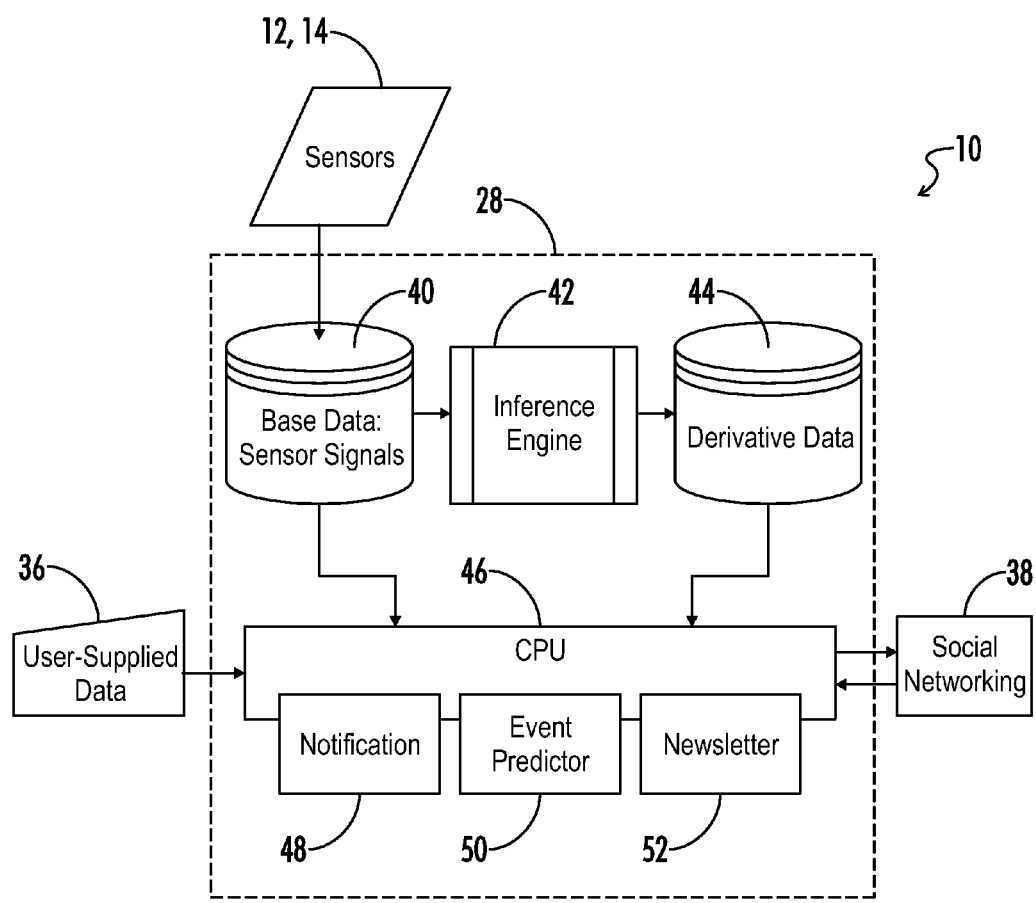
FIG. 2 is a block diagram representing exemplary program modules, engines and associated process flow for a system according to the present invention.

Referring more particularly first to FIGS. 1 and 2, an exemplary embodiment of a host system according to the present disclosure (e.g., a Smart Remote Monitoring System) may reside on a central server 28 and include one or more data processors 46 and computer-readable media functionally linked via a communications network 26 to a plurality of sensors 12, 14 as data sources. One primary market for the host system as disclosed herein may be senior citizens, but one of skill in the art may appreciate that the functions described herein may be more broadly applied to any individual requiring a professional or non-skilled caregiver, as well as to total population health applications.

The term "communications network" as used herein with respect to data communication between two or more parties or otherwise between communications network interfaces associated with two or more parties may refer to any one of, or a combination of any two or more of, telecommunications networks (whether wired, wireless, cellular or the like), a global network such as the Internet, local networks, network links, Internet Service Providers (ISP's), and intermediate communication interfaces.

The term "user interface" as used herein may unless otherwise stated include any input-output module with respect to the hosted server including but not limited to web portals, such as individual web pages or those collectively defining a hosted website, mobile desktop applications, telephony interfaces such as interactive voice response (IVR), and the like. Such interfaces may in a broader sense include pop-ups or links to third party websites for the purpose of further accessing and/or integrating associated materials, data or program functions via the hosted system and in accordance with methods of the present disclosure.

An exemplary host system, such as for example a Smart Remote Monitoring System ("Smart-RMS") as represented in FIG. 2, may without otherwise expressly limiting the scope of the present disclosure be a system for monitoring, gathering and analyzing data collected from or within a remote monitoring device network. The system generally uses an array of sensors and devices 12, 14 communicatively linked to a host server 28 to collect base data 40 associated with a subject (i.e., patient, senior, or other individual being monitored) within a given area. The data collection process by the sensors may be conducted in an entirely passive manner, meaning that it requires no conscious activity from the subject unless specifically noted herein. The base data 40 may be run through an inference engine 42 that generates derivative data 44. A series of algorithms may be executed by data processors 46 to utilize the base and derivative data and enable system capabilities, including but not limited to event notification 48, event prediction 50, and reporting 52.

More particularly with reference to FIG. 1, in one embodiment a host system 10 combines a device 12 for reporting activities of daily living with a biometric reporting device 14. These two separate devices and accompanying sensors may in various embodiments be joined to utilize a single network over which both types of data can be sent, thereby establishing a more comprehensive smart remote monitoring system 10. A daily living activity report device 12 for a system 10 as represented in FIG. 1 may receive a number of for example RF signals 16 representing the current status of subject activity. Exemplary activity sensors for implementation by a daily living activity reporting device 12 may include without limitation motion detectors, door contacts, flood (flush) detectors, pressure sensors (for bed and chair), Personal Emergency Response Systems (PERS) which require conscious activity, Active PERS which may (but not necessarily) be triggered by conscious activity, smoke detectors, carbon monoxide detectors, and the like.

The biometric device 14 may include or otherwise support inputs from designated medical devices using protocols such as Bluetooth 18, WiFi 20, ANT+ 22, or WWAN 24, any one or more of the inputs indicating a respective biometric status for the subject. Biometric input data may be provided from devices including without limitation blood pressure cuffs, weight scales, glucose meters, pulse/oximeters, and the like.

The base data 40 from the various sensors may further be associated with or otherwise be stored in the system corresponding to time and date stamps and/or equivalent information.

The devices 12, 14 may be coupled to a sensor communications hub (not shown) that is further linked to the server 28 via the communications network 26. The server 28 further may be communicatively linked via graphical user interfaces generated for or otherwise on behalf of for example healthcare professionals 30, subjects 32 and associated payors 34.

In an exemplary embodiment, the biometric reporting device may include or otherwise implement a Qualcomm 2Net® hub, and the activity reporting device may include or otherwise implement functionality from Resolution Products. The addition of the Resolution Products hub extends the capabilities of the 2net hub to include receiving and transmitting RF signals, which the 2net hub does not otherwise do. It may be understood that other devices may in certain embodiments be utilized to accomplish the same or equivalent features, and the examples shown and described herein may be considered as illustrative in nature, rather than limiting on the scope of the present disclosure.

The system generally, and more particularly the generation of derivative data for the purpose of implementing algorithms as disclosed herein, may optionally be enhanced through the use of user-input data 36 and social networking-generated data 38. These data sets are used in aggregate and in various combinations to enable features according to various embodiments of the present disclosure. In an embodiment, the host system may be integrated with one or more social media accounts. The integration of social media with the host system may be provided passively based on data and thresholds stored in association with the system. No direct action is necessarily taken by the subject in order to initiate the post. Rather, specific base and/or derivative data are flagged to be presented within social media accounts on behalf of the subject based on either an instance of the data (i.e. a PERS button push), or an established threshold(s) for the data (i.e. Amount of time out of bed exceeded, Number of pantry accesses exceeded, etc.).

The system optionally enables status updates to be made to the account by caregivers. These updates may in various embodiments be uploaded directly via a hosted web portal, e-mail, SMS text or directly through social media applications or other digital communications.

In typical implementations, the subject has no access to directly post to the social media accounts which are being posted on their behalf. Optionally, the subject may be accorded access to the account to post. Exemplary logic for an associated algorithm may include: If [NOTE ENTERED BY CAREGIVER], then [APPEND TO CARE NOTES], wherein caregiver notes may be System-Generated Alerts.

In various embodiments, an algorithm/program module of the system according to the present disclosure may take the aggregated ADL data and the derivative inferences and aggregate them into a periodic snapshot of the data. These "newsletters" serve as a baseline and record of the evolution of the senior's ADL over time. In one embodiment, the newsletter may be customized by the presenter or may be customized by the recipient. In an embodiment, the newsletter may give higher priority in presentation of data (base or derived) that falls outside of established parameters for norms/standards. In an embodiment, the newsletter may provide status updates regarding the integration of the passively-generated social media.

Exemplary logic for prioritizing presentation of data may include without limitation:
  If [DATA VALUE]<>[ESTABLISHED PARAMETERS], then [ASSIGN HIGHER PRIORITY]

In an embodiment, the host system of the present disclosure may serve as a time clock allowing caregivers to clock in and clock out with the addition of an input device (i.e. PC, smartphone, tablet, etc.). This function may optionally use a PIN or other unique ID code to protect against fraudulent entry. A "hyper-validation" feature may be used during a period of time during which a caregiver has been reported and/or is scheduled to be on site and/or a caregiver has logged in. An associated "EVV Hyper-validation" algorithm analyzes motion sensors, door contacts and other devices within the monitoring area for simultaneous signals that overlap (i.e. are received with the same or nearly the same time/date stamp) to determine if the monitoring area is occupied by more than the number of persons for whom care is being provided. Exemplary logic may include without limitation:
  With Log In
    If [EVV LOGIN] AND [NO EVV LOGOUT] AND THEN [PERIMETER ACTIVITY] AND [SIMULTANEOUS ACTIVITY], then [HYPER-VERIFICATION=TRUE]
    If [EVV LOGIN] AND [NO EVV LOGOUT] AND [PERIMETER ACTIVITY] AND [NO SIMULTANEOUS ACTIVITY], then [HYPER-VERIFICATION=FALSE]
  Without Log In
    If [PERIMETER ACTIVITY] AND THEN [SIMULTANEOUS ACTIVITY], then [HYPER-VERIFICATION=TRUE]

In an embodiment, a system according to the present disclosure may require a caregiver who has logged in to respond to a series of questions for the purpose of determining that the person was on site and/or for the purpose of ADL assessment and/or medical assessment. The type of validation can be geared to the specific skills attributed to the caregiver. For example, a skilled nurse may be presented with healthcare questions that are of a more measured nature.

In various embodiments, the system includes a set of derivative data that may be used for validating responses to systems requiring data input by the senior and/or by a caregiver. Systems may ask questions and compare the input responses to known values based on base and/or derivative data sets, including but not limited to those related to, e.g., sleep time, toilet usage, pantry/refrigerator access, time spent in an area or outside of an area, frequency of activity and/or an activity, compliance (i.e. wearing of a PERS device), etc. Exemplary logic may include without limitation:
  If [INPUT_RESPONSE]=[BASE_DATA VALUE], then [VALIDATE]
  If [INPUT_RESPONSE]=[DERIVED_DATA VALUE], then [VALIDATE]

An exemplary method as may be implemented by a host system according to the present disclosure generally begins with or otherwise includes generally steps for receiving base data from biometric and living activity sensors, and profile data for a particular subject. The profile data may be provided from any number of sources including but not limited to user input, social networking, medical records, and the like. Generally speaking, the profile data may further include a list of conditions for which the subject is considered to be at-risk or otherwise for which the subject should be directly monitored. This may be determined by the system based on the age, medical history, pharmaceutical history, demographics, etc., of the subject, or may be directly provided from one or more caregivers or even for example authorized family members.

In one exemplary embodiment, the host system further includes or has access to databases or equivalent data repositories wherein various conditions are further associated with predetermined event determination sequences. In other words, the system may effectively leverage stored data to determine the actual or likely presence of an event based on the input data in real-time from biometric and activity sensors, further in comparison with a predetermined sequence of one or more data points as determinative of an event and likewise a condition for which the subject is considered at-risk. As one example, a particular data point (subject opens front door at a given time) may be a primary data point in that is directly monitored and quantified, whereas this data point may take on more relevance in the context of the time itself (e.g., 2 o'clock in the morning) and the at-risk condition of a particular subject (e.g., one at risk of dementia).

An exemplary analytics process based on primary data points and with respect to time may include a measure of the amount of time spent in an area (i.e. room, bed, chair) on a daily basis, e.g., in X minute intervals. Another exemplary analytics process may include a measure of the number of times an area (i.e. room, bed, chair) was "in use" during a given measure of time. Another exemplary analytics process may capture the number of defined time periods (i.e. every 5, 10 or 15 minutes) during which activity was detected in an area (i.e. room, bed, chair) relative to another given time period (i.e. daily, awake hours, bedtime hours). Yet another exemplary analytics process may measure the frequency an area (i.e. room, bed, chair) was "in use" relative to other areas. As further disclosed herein, the combination of primary data points and program algorithms may generally be provided for basic monitoring, high risk situations, post-event monitoring, identifying relevant trends, triggering intervention or emergency response alerts and further generally supplement the subject profile for future diagnostics.

Various examples of even identification and extrapolation in the context of generating intervention alerts may be described next with reference to FIGS. 4-8. The term "intervention" in the context of the algorithms disclosed herein may unless otherwise stated define a prompt for intervention made to a caregiver or other person/agency with the authority to act in the best interest of the subject. This prompt may be issued by various methods including but not limited to an alarm, an SMS, e-mail, posting on a web site, phone call or other means of communication.

Figure 4:
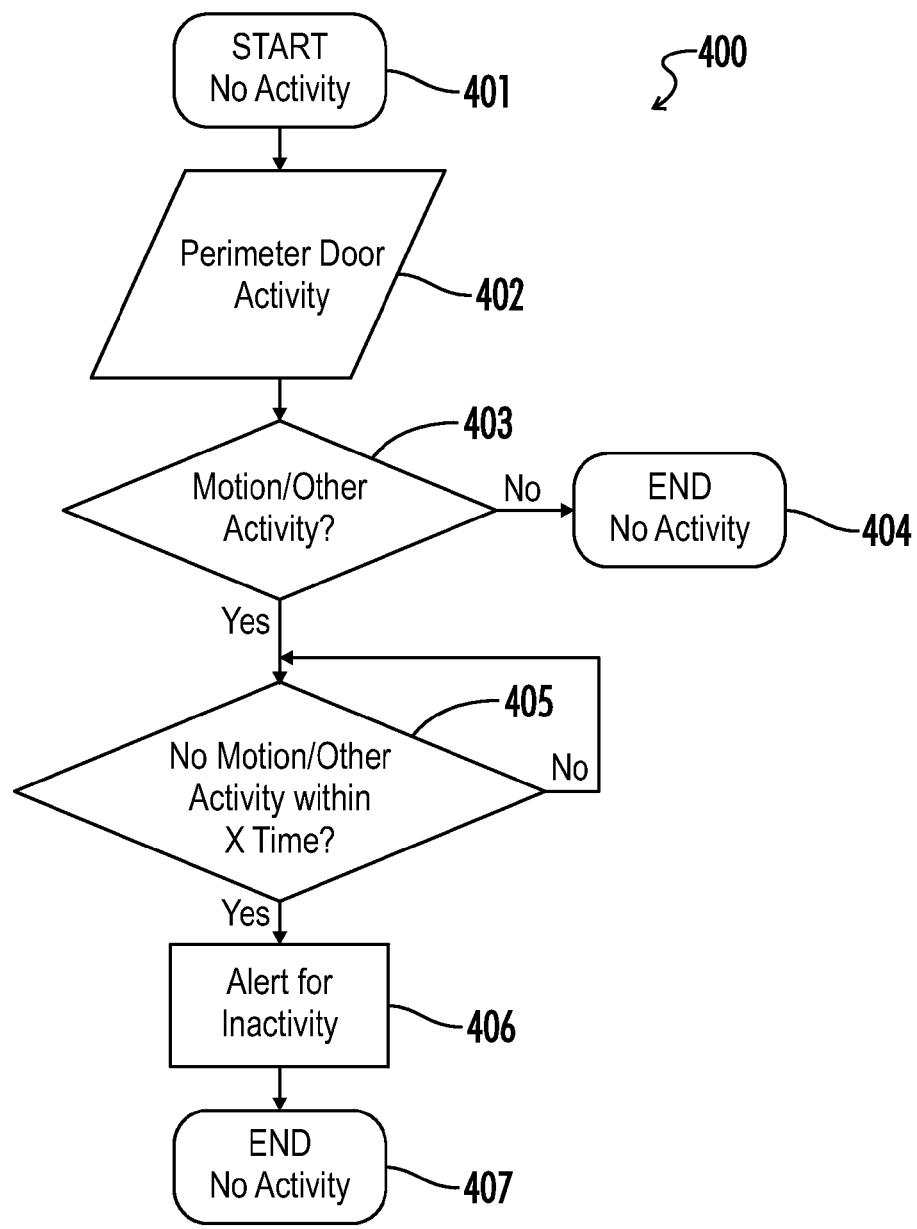
FIG. 4 is a flowchart representing an exemplary activity detection process performed by a system of the present invention.

Referring to FIG. 4, the system in one embodiment may perform diagnostics on input data to alert a caregiver to a potentially life threatening event warnings based on lack of activity during a defined period of known activity. An exemplary "No Activity" algorithm in accordance with this embodiment may monitor a combination of motion, door contact and/or pressure pad sensors in a target space for a lapse in activity during what is typically a time of activity. Parameters may be set and/or inferred (e.g., based on predetermined criteria and/or machine learning algorithms) to determine an acceptable period of activity to accommodate napping or other non-emergent situations. An example of the base logic may include the following:

If [NO PERIMETER ACTIVITY SINCE HISTORIC ACTIVITY] AND [NO ACTIVITY] for [TIME], then [INTERVENTION]

Exemplary derivative data used and/or generated may include a "last historic activity," i.e., establishing a time at which the last activity was detected other than perimeter door activity. A further exemplary "Perimeter Activity" algorithm (not shown) may utilize a door/window contact(s) to monitor a senior's home for a breach of the exterior. The primary algorithm functions during bedtime hours which can be a derivative and/or user input value.

Figure 5:
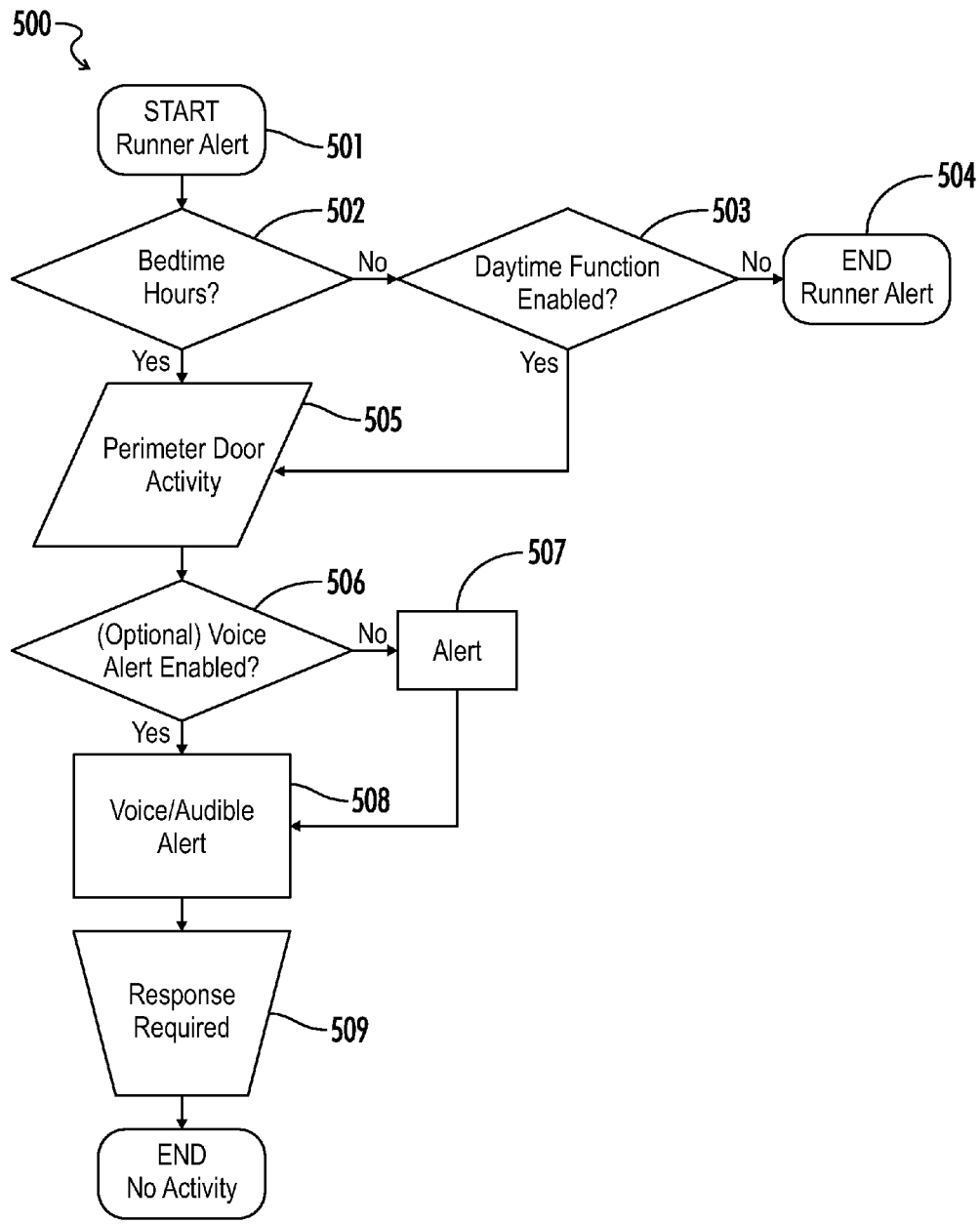
FIG. 5 is a flowchart representing an exemplary runner alert process performed by a system of the present invention.

Referring to FIG. 5, the system in one embodiment may perform diagnostics on input data to alert a caregiver if a perimeter breach occurs during a time deemed unacceptable. An enhanced algorithm with "Runner Alert" algorithms may further encompass non-bedtime hours as well (e.g., step 503), and may include an audible voice warning. This function may be used to monitor for "Runners" or "Wandering" as associated with dementia or other health issues. An example of the base logic may include the following:

If [BED TIME HOURS] AND [PERIMETER ACTIVITY], then [INTERVENTION].

This function can be enhanced to include a verbal or otherwise audible warning for a caregiver with responsibility for the patient (e.g., steps 506, 508). When enabled, the Dementia Enhancement would emit a verbal warning that a perimeter breach had occurred. Exemplary logic with dementia enhancement may include:

If [PERIMETER ACTIVITY], then [AUDIBLE WARNING] AND/OR [INTERVENTION].

Exemplary derivative data used and/or generated may include a "sleeping time," e.g., a measure of the amount of time slept based on a bed being occupied, and may be aggregated into time periods by day, week, month, and/or day of week. This function can be optionally enhanced with the inclusion of motion detection sensor data indicating activity in the room.

A "Pantry Activity" algorithm (not shown) may be provided which utilizes a sensor (door contact and/or motion detector) to quantify the volume and frequency of access to, e.g., one or more pantry/cupboard(s) and/or a refrigerator.

Derivative historical values and/or input values may in various embodiments establish thresholds utilized by a system and method as disclosed herein to identify trends and/or variations in eating habits. Significant variations or breaches of thresholds may result in prompt(s) for intervention being issued. Alternatively, thresholds may be established and prompts for intervention issued when thresholds are breached. This function may be utilized to, e.g., identify and monitor dietary habits, identify/diagnose overeating, malnourishment or other eating disorders, identify/diagnose other health-related issues that have sleep disorder as a symptom, monitor other health-related issues that have sleep disorder as a symptom, or the like.

Exemplary derivative data used and/or generated may include "Pantry Raid or Neglect" data, wherein the system measures the number of times a pantry or other food storage area was accessed within a given time period (i.e. daily, weekly, during awake hours, during bedtime hours). The data may be constrained to absolute indicators of access or aggregated by instances of access within a time period (i.e. 5, 10, 15 minute intervals). The "Pantry raid or Neglect" data may be calculated with respect to various time periods including but not limited to: time of day, meal times, day, week, day of week, etc.

A "Nighttime Pantry Access" algorithm (not shown) may be provided which cross-references derivative and/or input values for the bedtime hours with "Pantry Access" data to identify nighttime eating habits.

Figure 6:
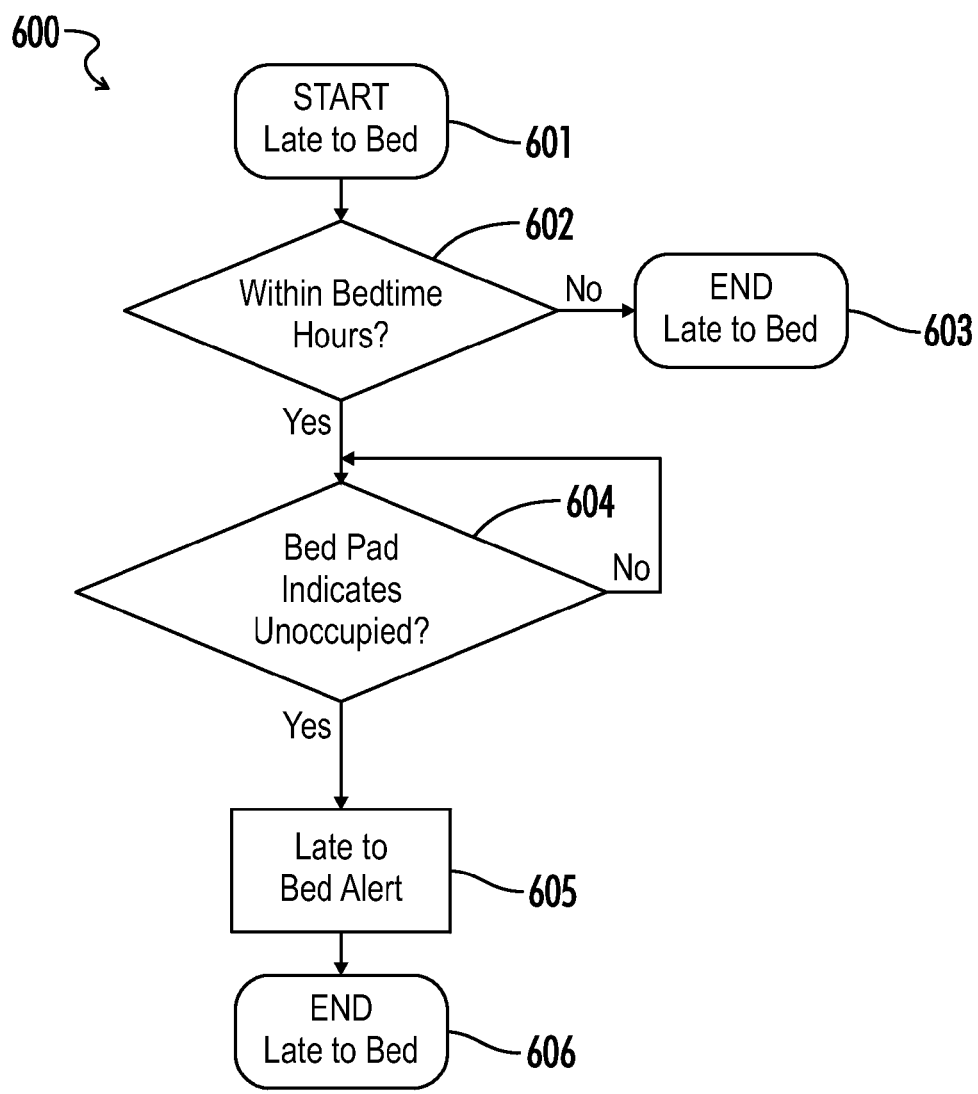
FIG. 6 is a flowchart representing an exemplary "late to bed" monitoring process performed by a system of the present invention.

Referring to FIG. 6, the system in one embodiment may perform diagnostics on input data to alert a caregiver if a subject is late to bed. A "Late to Bed" algorithm may be provided which in conjunction with appropriate sensors and communication network components may be executed to monitor the bed pressure pad, to determine instances where a senior may be late getting to bed, and to determine the acceptable late time period(s). The "late to bed" algorithm establishes a variable(s) that is learned and modified over time as sleep habits change and/or evolve. It can be initialized, overridden and/or enhanced with user input data. This function may be utilized to, e.g., identify and monitor general sleep habits, sleep disorders, other health-related issues that have sleep disorder as a symptom, etc. An example of the base logic may include the following:

If [BED NOT OCCUPIED] AND [LATEST TIME TO BED], then [INTERVENTION]

If [BED NOT OCCUPIED] AND [LATEST TIME TO BED] AND [NO ACTIVITY], then [INTERVENTION]

Figure 8:
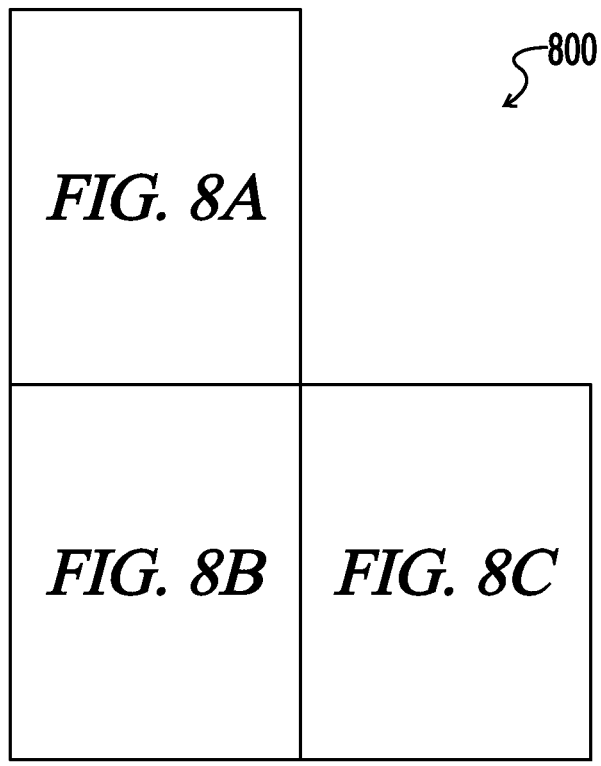
FIG. 8 is a block diagram representing portions of a flowchart as described below with respect to FIGS. 8A to 8C.

This function may in various embodiments be further used for the purpose of determining an appropriate time to enable a "Fall Detection by Logic" algorithm, as described in greater detail below and with reference to FIG. 8.

Exemplary derivative data used and/or generated may include "Time to Bed" data, which captures the time at which a bed is initially occupied each evening and may be aggregated for analysis by day, week, month and/or day of week. Further exemplary derivative data may include "Latest Time to Bed" data, as a calculated value that determines expected variations in a person's going to bed time based on historical values for day, week, month and/or day of week.

Figure 7:
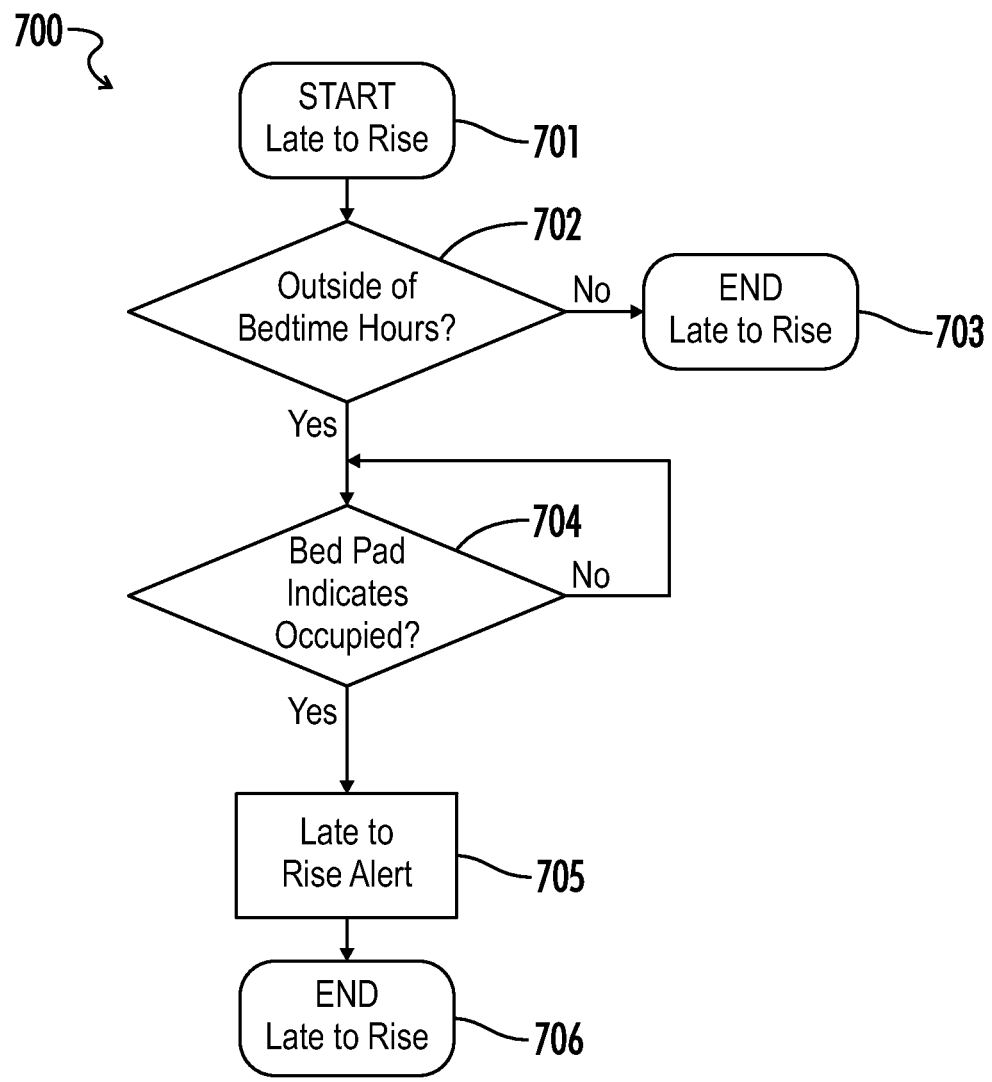
FIG. 7 is a flowchart representing an exemplary "late to rise" monitoring process performed by a system of the present invention.

Referring to FIG. 7, the system in one embodiment may perform diagnostics on input data to alert a caregiver if a subject is late to rise. A "Late to Rise" or "Snooze" algorithm may be provided which monitors the bed pressure pad to determine instances where a senior may be late to arise from the bed and determines the acceptable late time period(s). The Snooze algorithm establishes a variable(s) that is learned and modified over time as sleep habits change and/or evolve. The function can be calibrated by day of week, time of year, etc. An example of the base logic may include the following:

If [BED OCCUPIED] AND [AFTER TIME TO RISE+ SNOOZE], then [INTERVENTION]

If [BED NOT OCCUPIED] AND [AFTER TIME TO BED] AND [NO ACTIVITY], then [INTERVENTION]

Exemplary derivative data used and/or generated may include "time to rise" data which captures the time at which a bed is initially vacated each morning and may be aggregated for analysis by day, week, month and/or day of week. Further exemplary derivative data may include "snooze" data as a calculated value that determines expected variations in a person's waking time based on historical values for day, week, month and/or day of week.

A "Variation in Sleep Time" algorithm (not shown) may be provided which determines if a senior's amount of sleep is varying. Historical values are compared against current individual and/or aggregate values to determine deviations. An example of the base logic may include the following:

If [CURRENT WEEK SLEEP TIME]<>[CURRENT WEEK-1 SLEEP TIME], then [SLEEPING LONGER ALERT]

If [CURRENT WEEK SLEEP TIME]<>[CURRENT WEEK-2 SLEEP TIME], then [SLEEPING LONGER ALERT]

If [CURRENT WEEK SLEEP TIME]<>[CURRENT WEEK-3 SLEEP TIME], then [SLEEPING LONGER ALERT]

If [CURRENT WEEK SLEEP TIME]<>[CURRENT WEEK-4 SLEEP TIME], then [SLEEPING LONGER ALERT]

Figure 8A:
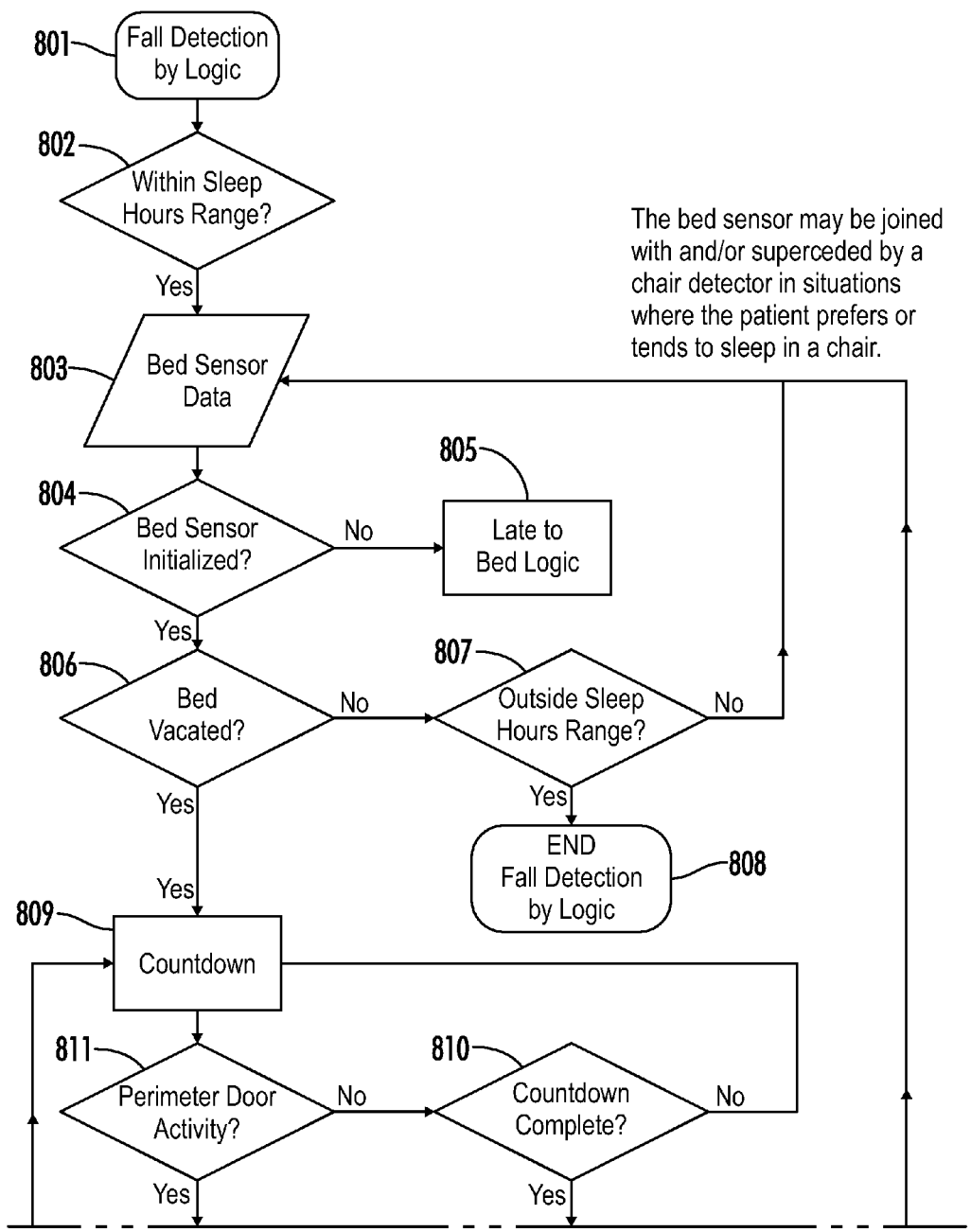
FIG. 8A is a flowchart representing a first portion of an exemplary "fall detection by logic" process performed by a system of the present invention.
Figure 8B:
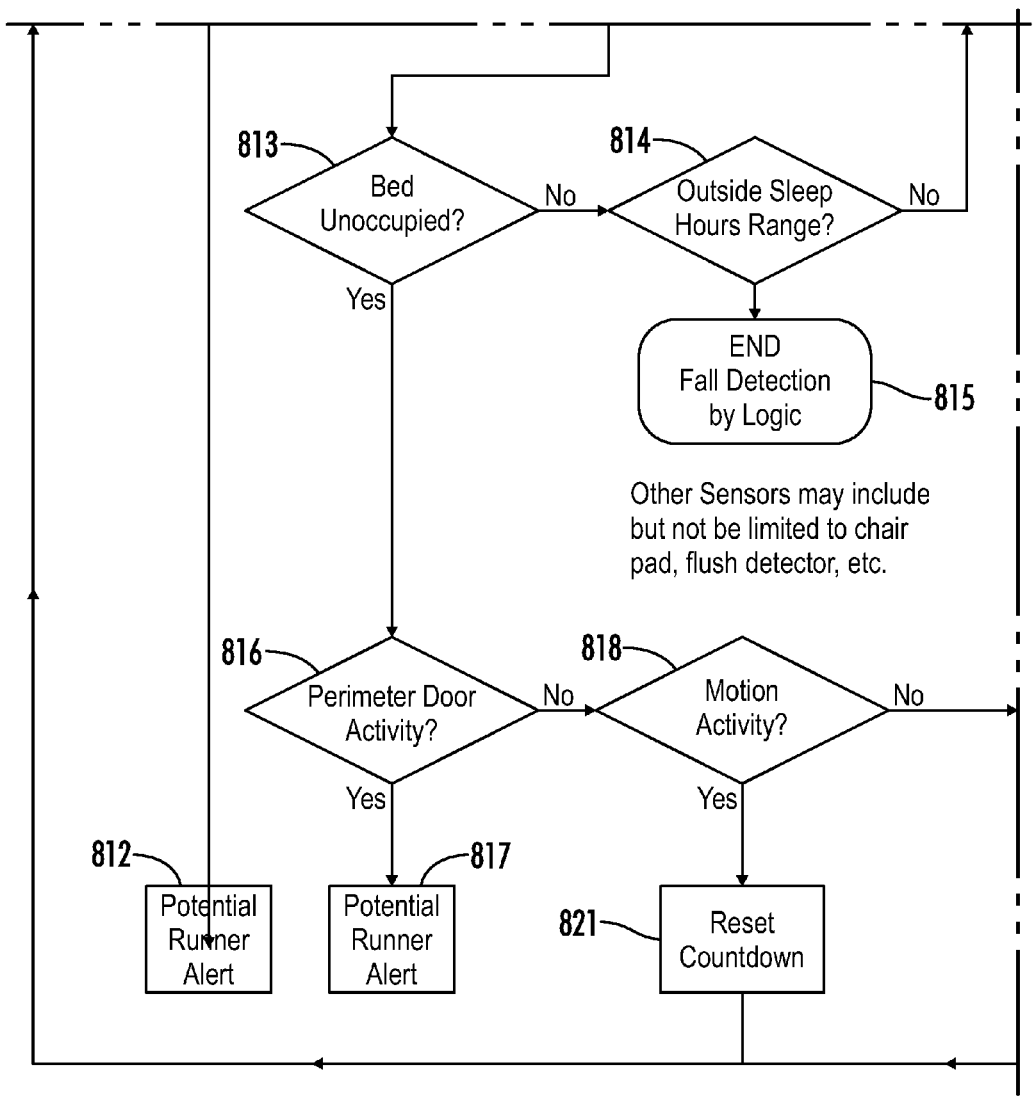
FIG. 8B is a flowchart representing a second portion of an exemplary "fall detection by logic" process performed by a system of the present invention.
Figure 8C:
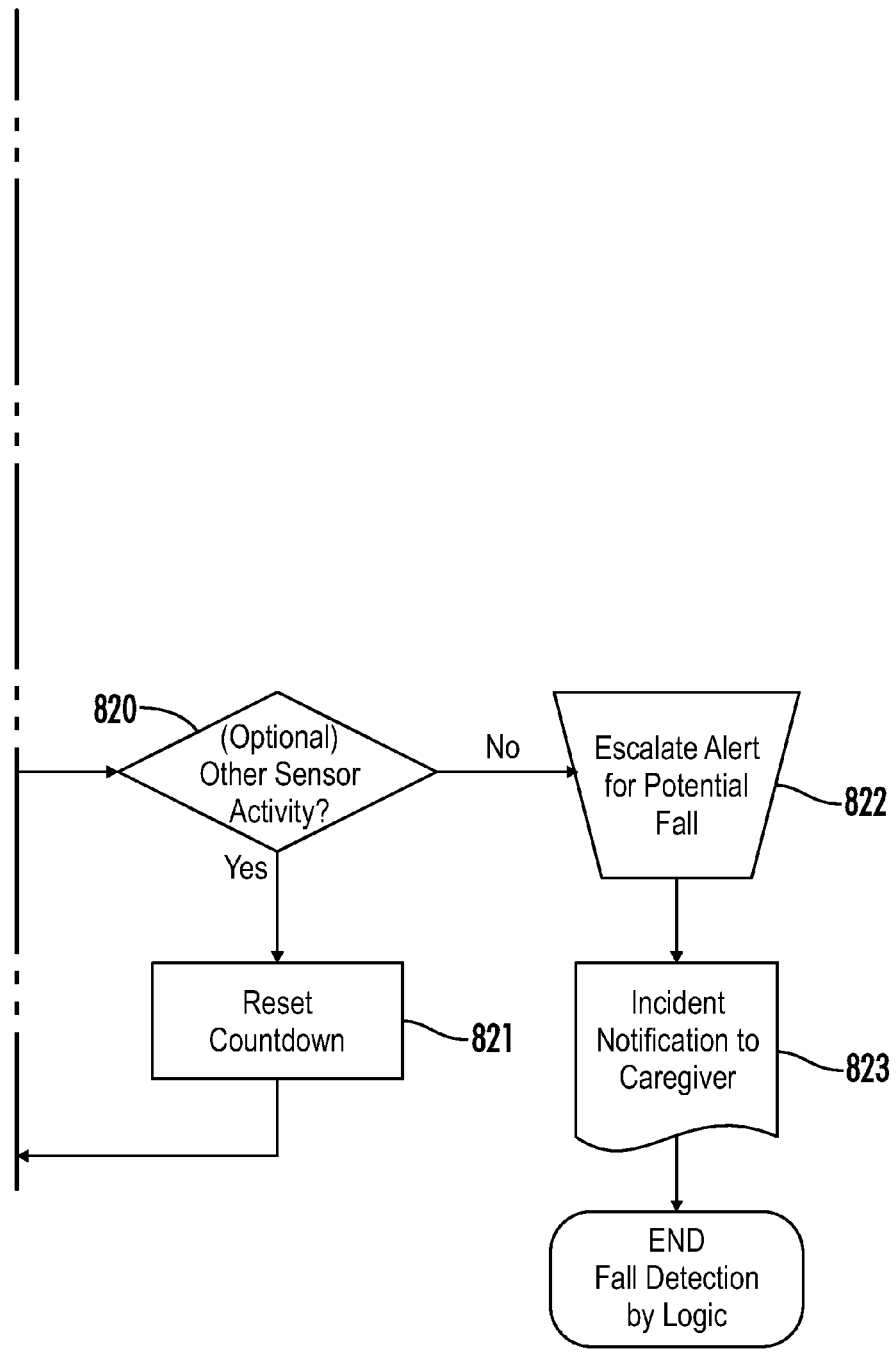
FIG. 8C is a flowchart representing a third portion of an exemplary "fall detection by logic" process performed by a system of the present invention.

Referring to FIGS. 8A to 8C, the system in one embodiment may perform diagnostics on input data to offer nighttime fall detection without the need for a Personal Emergency Response System (PERS) or other notification device. A "Fall Detection by Logic" algorithm determines if a potential nighttime fall has occurred. The algorithm monitors the bed pressure pad during sleeping hours for periods of vacancy accompanied by a lack of activity from other sensors to indicate that a subject may have fallen. The addition of an Active PERS device may allow this algorithm's functional time period to be extended to cover periods of time when the Active PERS device is not being worn. This function may be utilized to, e.g., monitor for and identify falls, comprehensively capturing nighttime falls including those that previously may have gone unreported. Falls may further be determined in combination with a "no activity" algorithm as previously described.

Additionally, an Active PERS device in various embodiments comprehensively captures instances of falls outside of the fall detection by logic algorithm including those that previously may have gone unreported. The indication of a fall by any one or more of the Fall Detection by Logic, No Activity and Active PERS may be used to cross-validate in instances where a fall is detected by more than one method. For added accuracy, detected falls may be confirmed individually or collectively through communication with the senior, insurance claims, medical records, caregiver communication or other means. Collectively or individually, these captured falls may be used to predict future falls.

In its most raw form, detected falls are aggregated and used as a means to indicate a predisposition for future falls. This is a methodology consistent with the fall scoring as currently known in the art, but is more accurate than the current method which currently depends on self-reported incidences which represent less than 50% of the actual incidences. A system according to the present disclosure may anticipate future falls based on the comprehensive data set and allow additional and more severe subsequent falls to be monitored, minimized and/or averted through intervention and/or previous knowledge of a patient in an at risk situation.

In various embodiments, a "Fallcasting" algorithm (not shown) may quantify by amount of time of inactivity following a fall event utilizing other sensors in the home such as motion detectors, door contacts, chair pads and bed pads. These periods of inactivity are used to calculate the severity of a captured fall(s) and are factored into the likelihood of a future fall(s) and the severity of that/those future fall(s). This algorithm may typically compare an individual's data to established benchmarks among control groups.

Another more advanced algorithm may be provided or otherwise implemented which utilizes the activity score provided by the Active PERS device to compare the relative activity level of the senior pre- and post-fall event. This scoring may be used by clinicians and/or health plans to prioritize the need for intervention where a significantly lower score post-event is indicative of a higher need for intervention such as physical therapy (e.g.). This algorithm compares a patient's relative individual scores and/or compares the relative scores to established benchmarks among control groups.

Activity scores post-event may be evaluated among groups (demographic, regionally, by health plan, etc.) as well as relatively among other defined groupings. The system may further calculate the number of falls preceding a hospitalization due to a fall. This data is applied against demographic data (including but not limited to age, gender, geographic location, diseases, co-morbidities, race, etc.) to determine if a greater likelihood of a fall exists for an individual based on their demographic profile.

While this alert is generally deployed during bedtime hours, it can be manually extended to provide more comprehensive coverage. An example of the base logic may include the following:

If [NO PERIMETER ACTIVITY] AND [BEDTIME HOURS] AND [BED VACATED] AND [TIME ELAPSED] AND [ACTIVITY], THEN [RESET TIMER]

If [NO PERIMETER ACTIVITY] AND [BEDTIME HOURS] AND [BED VACATED] AND [TIME ELAPSED] AND [NO ACTIVITY], THEN [INTERVENTION]

This could be done with the second portion as an ELSE option.

Exemplary derivative data used and/or generated may include "time to bed" data which captures the time at which a bed is initially occupied each evening and may be aggregated for analysis by day, week, month and/or day of week. Further exemplary derivative data may include "latest time to bed" data as a calculated value that determines expected variations in a person's going to bed time based on historical values for day, week, month and/or day of week. Further exemplary derivative data may include "time to rise" data which captures the time at which a bed is initially vacated each morning and may be aggregated for analysis by day, week, month and/or day of week. Further exemplary derivative data may include "snooze" data as a calculated value that determines expected variations in a person's waking time based on historical values for day, week, month and/or day of week. Further exemplary derivative data may include "nightly toilet usage" data as a detected daily, weekly, monthly aggregate number of instances of toilet usage during bedtime hours. Further exemplary derivative data may include "inferred nightly toilet use" as a determined daily, weekly, monthly aggregate number of instances of toilet usage during bedtime hours based on number of times a bed is vacated. The data may be enhanced through elimination of instances of vacated bed when sensors detect other activity (i.e. kitchen motion). The data may further be enhanced to constrain number of instances within a given time period (i.e. 5, 10, 15 minutes).

A "toilet use" algorithm (not shown) may be provided in accordance with the present disclosure which utilizes the bed pressure pad and/or the flood/flush detector to monitor bathroom usage. For nighttime, a bed pad indicating that the bed has been vacated during sleep time hours is the core indicator. The addition of the flush monitor enhances the ability of the algorithm to predict that bathroom usage is the reason for vacating the bed. This function may be utilized to, e.g., monitor and identify for incontinence or related-health issues such as potential falls, bladder infection, etc. This feature may further enhance the logic of the Fall Detection by Logic algorithm. An example of the associated logic may include the following:

If [BEDTIME HOURS] AND [BED VACATED], then [INFERRED TOILET USE +1]

If [BEDTIME HOURS] AND [BED VACATED] AND [TOILET FLUSH], then [TOILET USE +1]

If [BEDTIME HOURS] AND [BED VACATED] AND [BATHROOM MOTION], then [TOILET USE +1]

If [BEDTIME HOURS] AND [BED VACATED] AND [TOILET FLUSH] AND/OR [BATHROOM MOTION], then [TOILET USE +1]

As referred to above, an Active PERS device typically utilizes an accelerometer to "score" movements. Movements that exceed a certain threshold are considered to be indicative of a fall. An Active PERS device has a "reporting threshold" that can be modified to account for the level of activity by the wearer. The threshold is necessary to avoid false positives and account for the wearer's level of activity. Scores below the reporting threshold are not reported (i.e. sent for intervention).

In an embodiment of the present disclosure, a "Remind to Wear" algorithm monitors for compliance to ensure that the subject wears the device. Logic may be added to the device to detect periods of prolonged inactivity. Long periods of inactivity generate a prompt for intervention by the Active PERS device. The "Remind to Wear" algorithm prompts an alert to remind the wearer to wear their Active PERS device. The prompt may be actualized via e-mail, text, or other digital delivery method and/or phone call (automated or personalized). The "Remind to Wear" algorithm further filters the prompts to account for sleeping hours to avoid false positives. An example of the base logic may include the following:

If [NOT BEDTIME HOURS] AND [NO MOTION ACTIVE_PERS], then [INTERVENTION]

In an embodiment, an "Activity Scoring Active PERS" algorithm requires the "reporting threshold" be set lower to capture more of a wearer's daily activity. The algorithm filters the data for scores that are above the "fall detection threshold" to maintain the fall detection capability. The scores between the "reporting" and fall detection thresholds are used to generate a score indicating the level of activity of the wearer. The scores may be aggregated on different time periods which can be determined by a default value, a user input value or a learned value. The scores are presented as straight scores and/or are compared relative to one another to determine a change in the amount of the wearer's activity.

An "Activity Scoring" algorithm monitors the amount of activity exhibited by a senior within their ADL environment. Scoring can be done on an absolute, relative or mixed scoring basis. Activity is defined as motion logged via the motion detectors. Multiple signals of motion from alternating motion detectors would increase the rating. For subjects confined or primarily confined to an area, the activity score would be an absolute value. For seniors who leave the premises, scoring would be on a relative basis comparing one day to the next and accounting for time away as a period of assumed activity. While the activity outside of the home is not measured, the time spent outside of the home is assumed to include some activity on the senior's part. Exterior door openings where the senior can be logically deduced to have left the premises may be factored in.

The baseline value is established by user input values and/or learned values. A historical record of the activity is logged for subsequent analysis. Subsequent analysis may include without limitation identifying fluctuations in activity, variations in timing of activity, or the like. Optionally, a subject and/or a caregiver may rate their activity for a given day. This rating may optionally be used to calibrate the system, assess the subject's awareness and/or self-awareness, or the like. Optionally, an Active PERS activity score is analyzed in conjunction with the Activity Score from motion detectors. Optionally, seasonal conditions including temperature and weather conditions are used to calibrate the system.

Various challenges and/or limitations may include interference or false readings created via non-seniors on premises such as family or caregivers. Time spent outdoors by the subject will by its very nature not be factored into the analytics. Weather could be a factor (i.e. inside more in winter and outside more in summer). Analytics blended with ACTIVE PERS Motion could also be implemented as desired.

In an embodiment, the system program engines may be configured to include functions based on a known senior disease state(s). These functions may be based on base data and/or derived data and/or the proprietary algorithms that evaluate that data. Some of these configurations may be as follows:

DEMENTIA
    If [DEMENTIA]=YES, AND [ACTIVITY=CONSTANT], then [WANDERING ALERT]
    If [PANTRY_ACCESS]<X, then [NOT EATING ALERT]
DIABETES
    If [DIABETES=YES] AND [CUPBOARD ACCESS]>X, then [INTERVENTION ALERT]
DEPRESSION
    If [DEPRESSION]=TRUE, AND [NO PERIMETER ACTIVITY WITHIN 24 HOURS], then [INTERVENTION ALERT]
    If [NO ACTIVITY WITHIN 24 HOURS], then [INTERVENTION ALERT]

In an embodiment, a system according to the present disclosure may implement a Vigilant Mode which minimizes or eliminates any tolerances in the system for Fall Detection or other monitoring. Exemplary logic may include without limitation:

If [OUT OF BED THIS WEEK>OUT OF BED LAST WEEK], then [VIGILANT MODE]

Using historical data, it is possible to identify and categorize significant events and their associated time of occurrence. An analysis or review may be conducted for data that fall outside of a baseline and to flag those as indicators for the event. In an embodiment, a system according to the present disclosure may include and implement a disease prediction module, wherein analytics may be conducted to predict diseases such as dementia (future), exemplary logic for which includes without limitation:

If [DEMENTIA=YES] AND [ACTIVITY=CONSTANT], then [WANDERING ALERT]

Pattern recognition may be an integral factor in various aspects, but in many cases this feature may be difficult to accurately model. In certain embodiments, the system may apply pattern recognition in some known settings and establish patterns.

If [NO CUPBOARD ACCESS] OR [NO FRIDGE ACCESS], then [NOT EATING ALERT]

Other examples of diseases according to such an embodiment may be diabetes, depression, frailty, etc., each having associated derivative data, base logic, etc.

In an embodiment, a system according to the present disclosure may include post-event learning and event prediction program modules, wherein following an event (fall, stroke, heart attack, etc.) data may be reverse analyzed to identify changes in the data that preceded the event. Each event may be categorized to capture event specific data including, but not limited to, a type of event (e.g., fall, stroke, heart attack, number of instances thereof, etc.), date/time of occurrence, severity, outcome (as known), and the like. Demographic data about the subject may be included as available, including, but not limited to age, gender, race, location, and health-related data demographic data such as ADL scores, health risk assessment data, and recorded biometric scores such as blood pressure, weight, glucose and pulse/oxygen.

In various embodiments, analysis may be conducted on base and derivative data sets beginning at the time of the event and working backward in the logged data sets until a consistent value for the data set is reached. That consistent value and its time from the point of the event are defined as the data set benchmarks. Benchmarks can be absolute values and/or ranges. A benchmark can also be established for a data set based on system defaults, user input values and/or learned values. Data may be analyzed and sorted by time from the benchmark point in terms of absolute (raw measure) and relative variation (i.e. percentage change) from the benchmark.

Typically, data sets may be of three types—indicator, early indicator and non-indicator. In general, indicator data a data set with variations that ultimately converge to a consistent value or range. In general, early indicator data is an indicator data set that manifests a deviation from the benchmark earliest (furthest from the event) are considered "early indicators" and are used to identify potential events. As such, Early Indicator Data Sets are a subset of the Indicator Data Sets. In general, non-indicator data is a data set with no consistent values and/or values that have no appreciable change.

With respect to an event prediction module as referred to above, in various embodiments deviations within a data set from the data set benchmark are used as generic event predictors. The benchmarks are based on system defaults, user input values and/or learned values over time. If a subject breaches any of these benchmarked thresholds, a prompt for intervention is issued.

Alternatively, when a subject has a previous event and/or a common demographic group has a previous event benchmarks are used to establish appropriate ranges for the subject. If these ranges are breached, a prompt for intervention in anticipation of a specific type of event is issued.

Prompts may be graded according to the number of early indicators and indicators occurring. Subsequent higher priority alerts are issued if thresholds continue to be breached and/or additional data set thresholds are breached. The established data sets may be used as baselines for a subject to predict the potential for an occurrence/recurrence of an event. First time occurrences are based on a group analysis. Recurrences are based on subject-specific analysis as well as common demographic group analysis.

Generally stated, a subject has data set benchmarks that are unique to them. Subject-specific analysis is run against these benchmarks, and breaches of early indicator and indicator thresholds result in the issuing of a prompt for intervention.

In various embodiments, subjects may be compared against other subjects based on single or multiple common demographic data elements. Data sets are aggregated to determine which data sets are the most accurate indicators for a type of event for a given demographic group.

A data set that has early indicator data may generally issue a prompt for intervention. The prompt for intervention is given higher priority based on the existence of other early indicators or indicators. The prompt for intervention is given a lower priority based on the absence of other early indicators or indicators.

In various embodiments, for both generic and event-specific prediction, the sensitivity of a prompt for intervention may be adjusted in a number of ways. As one example, the system may change the number of indicator data sets required to trigger the alert. Sensitivity may be adjusted based on the margin of deviation from the benchmark (either absolute or relative values), or by the length of time elapsed that data set benchmarks have been consistently breached, by demographic comparison that suggests a higher or lower rate of incidence for a subject's given demographic(s), or by a subject's previously recorded event history, etc.

Figure 3:
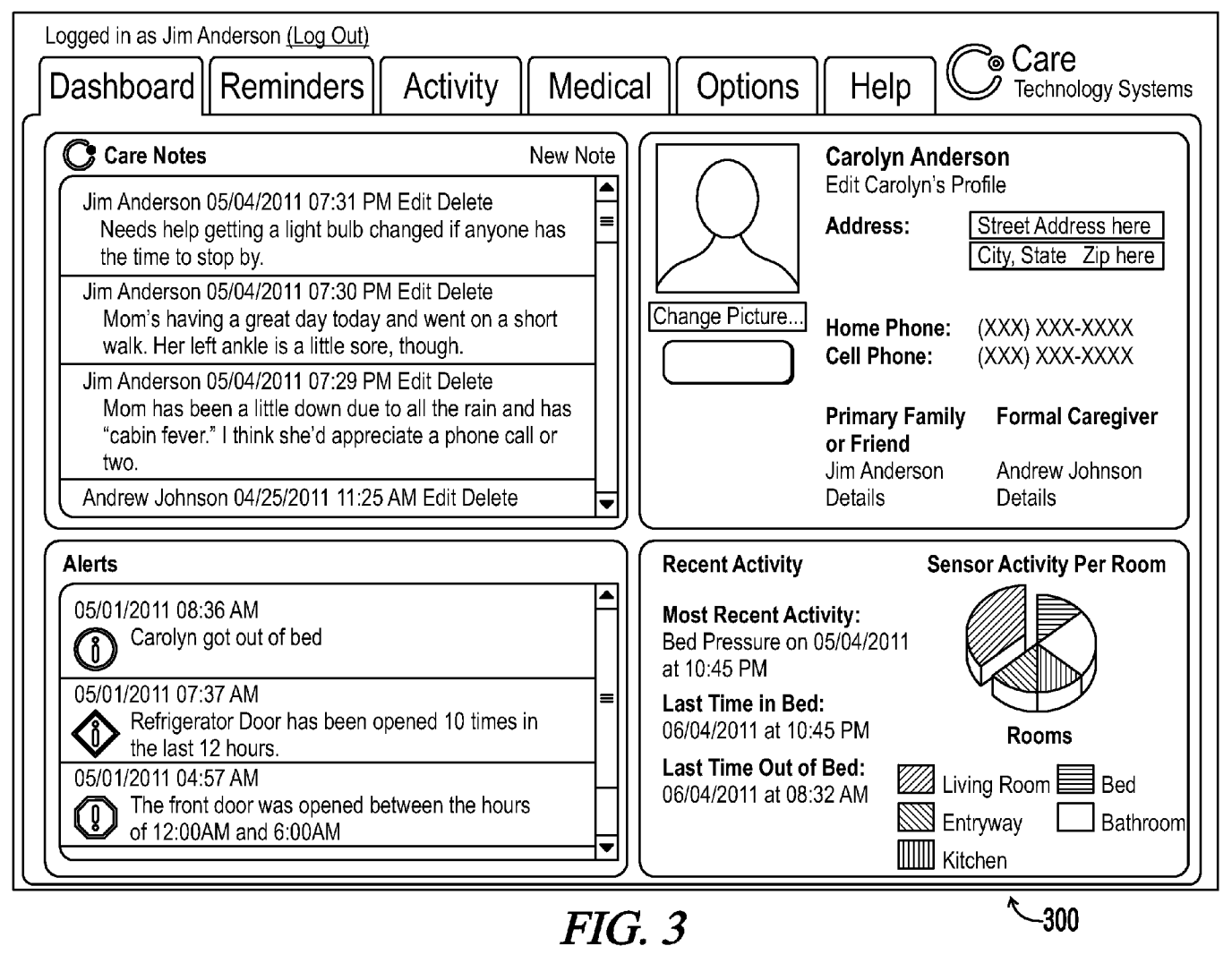

A system according to the present disclosure may generate and implement a user interface accessible via a communications network by remote users such as for example caregivers. An exemplary web-based version of the Caregiver Interface 300 as represented in FIG. 3 may be designed to provide the caregiver(s) with an easily interpreted view of the data and function within the system. Basic patient information appears in the top right quadrant of the Dashboard tab. This area displays the patient's name and other core information is displayed to confirm that the patient is the one associated with the caregiver. Recent Activity appears below that in the bottom right quadrant. This section displays some of the aggregated and derivative data from the system including but not limited to distribution of time spent in a given area, number of exterior/refrigerator/pantry door opens, trends in those distributions (time to bed, hours slept, door opens by day, etc.). Alerts, in the bottom left quadrant, are alerts presented in a color-coded system indicating whether those alerts are of low, moderate or high priority. These are system-generated alerts stemming from the fall detection by logic algorithm, late to bed, late to rise, and other system alerts as well as PERS activation alerts. Care Notes in the top left corner of the Dashboard tab shows the integration of social media with the system. Alerts are also incorporated into the Care Notes to provide a comprehensive record of the patient's daily activities.

The previous detailed description has been provided for the purposes of illustration and description. Thus, although there have been described particular embodiments of a System and Method of Automated Healthcare Assessments and Event Inferences, it is not intended that such references be construed as limitations upon the scope of an invention as disclosed herein except as set forth in the following claims.

What is claimed is:

1. A system for diagnosing and prompting healthcare interventions, the system comprising:
    a first set of one or more sensors disposed in a defined area and effective to generate output signals representative of biometric data for a healthcare subject;
    a second set of one or more sensors disposed in the defined area and effective to generate output signals representative of activity within the defined area;
    a server functionally linked via a communications network to the sensors and further comprising a data processor, a data storage network and a non-transitory computer-readable medium having program instructions residing thereon, the instructions executable by the processor to direct the performance of operations further comprising:
        storing base data comprising time-specific biometric and activity data points for the subject in the data storage network,
        determining derivative data comprising one or more inferred temporal relationships with respect to the base data;
        determining an event requiring intervention by comparing one or more combinations of base data and derivative data with associated intervention criteria comprising one or more of temporal ranges and threshold values;
        post-event monitoring of activity data to determine a severity of a respective event;
        aggregating data comprising one or more determined events, a determined severity of the events, and associated base data and derivative data in the data storage network;
        reverse analyzing post-event activity and pre-event activity represented by the aggregated data as predictive indicators of a future likelihood of such events and a likely severity of such events;
        dynamically adjusting one or more intervention criteria based on the predictive indicators; and
        delivering an intervention prompt to a healthcare provider associated with the subject, the intervention prompt prioritized based on a relative post-event activity level of the subject with respect to a pre-event activity level.

2. The system of claim 1, further comprising instructions executable to direct the performance of an operation of enabling users to provide input relevant to a healthcare profile for the subject, wherein an initial set of intervention criteria is defined based in part on the healthcare profile.

3. The system of claim 1, wherein intervention criteria associated with the subject are dynamically adjusted over time based on determined events and patterns in the stored base data and determined derivative data.

4. The system of claim 1, wherein one or more inferred temporal relationships as derivative data comprise an inferred period of inactivity with respect to at least a portion of the defined area.

5. The system of claim 1, wherein one or more inferred temporal relationships as derivative data comprise an inferred frequency of activity with respect to at least a portion of the defined area.

6. A system for diagnosing and prompting healthcare interventions, the system comprising:
    a set of one or more sensors disposed in a defined living area for a healthcare subject, the sensors effective to generate output signals representative of activity within the area;
    a server functionally linked via a communications network to the one or more sensors and further comprising a data processor, a data storage network and a non-transitory computer-readable medium having program instructions residing thereon, the instructions executable by the processor to direct the performance of operations further comprising:
        storing time-specific activity data points for the subject in the data storage network,
        determining derivative data comprising one or more inferred temporal relationships with respect to the activity data points;
        identifying one or more periods of inactivity in at least a portion of the defined area from the derivative data, the one or more periods of inactivity having at least a threshold duration;
        determining a fall by the subject wherein one or more of the identified periods of inactivity correspond to a period of expected activity;
        post-event monitoring of activity data point and derivative data to determine a severity of the fall;
        aggregating data comprising one or more determined falls, a determined severity of the respective falls, and associated base data and derivative data in the data storage network;
        reverse analyzing post-fall activity and pre-fall activity represented by the aggregated data as predictive indicators of a future likelihood of falls and a likely severity of such falls;
        dynamically adjusting one or more of the threshold duration for inactivity and the period of expected activity based on the predictive indicators; and
        delivering an intervention prompt to a healthcare provider associated with the subject, the intervention prompt prioritized based on a relative post-fall activity level of the subject with respect to a pre-fall activity level.

7. The system of claim 6, wherein the operation of identifying one or more periods of inactivity comprises identifying a lack of movement in the defined area for a first period of time and a lack of use in a defined sleeping area for the first period of time, the first period of time having a duration exceeding a threshold duration associated with determining a fall by the subject.

8. The system of claim 6, wherein the operation of identifying one or more periods of inactivity comprises identifying a lack of movement with respect to one or more of:
   a defined food storage area for a first period of time, the first period of time having a duration exceeding a threshold duration associated with determining an eating disorder for the subject, and
   a defined sleeping area for a second period of time, the second period of time having a duration exceeding a threshold duration associated with determining a sleeping disorder for the subject.

9. A system for diagnosing and prompting healthcare interventions, the system comprising:
   a set of one or more sensors disposed in a defined living area for a healthcare subject, the sensors effective to generate output signals representative of activity within the area;
   a server functionally linked via a communications network to the one or more sensors and further comprising a data processor, a data storage network and a non-transitory computer-readable medium having program instructions residing thereon, the instructions executable by the processor to direct the performance of operations further comprising:
      storing time-specific activity data points for the subject in the data storage network,
      determining derivative data comprising one or more inferred temporal relationships with respect to the activity data points;
      identifying a duration or frequency of activity with respect to at least a portion of the defined area from the derivative data;
      determining an event requiring intervention wherein the respective duration or frequency of activity exceeds a threshold value for the subject;
      post-event monitoring of activity data to determine a severity of the event;
      aggregating data comprising one or more determined events, a determined severity of the respective events, and associated base data and derivative data in the data storage network;
      reverse analyzing post-event activity and pre-event activity represented by the aggregated data as predictive indicators of a future likelihood of such events and a likely severity of such events;
      dynamically adjusting one or more of the threshold value for the respective duration and the threshold value for the frequency of activity, based on the predictive indicators; and
      delivering an intervention prompt to a healthcare provider associated with the subject, the intervention prompt prioritized based on a relative post-event activity level of the subject with respect to a pre-event activity level.

10. The system of claim 9, wherein the operation of identifying a duration or frequency of activity comprises identifying one or more breaches with respect to one or more perimeter portions of the defined area during an expected sleeping time associated with the subject.

11. The system of claim 10, further comprising instructions executable to direct the performance of operations of
   aggregating data comprising determined breaches, associated activity data and associated derivative data in the data storage network, and
   implementing the aggregated data as predictive indicators of future breaches.

12. The system of claim 9, wherein the operation of identifying a duration or frequency of activity comprises identifying a frequency of access to a defined food storage area over a first period of time, the identified frequency exceeding a threshold value associated with determining an eating disorder for the subject.

13. The system of claim 9, wherein the operation of identifying a duration or frequency of activity comprises identifying use of a defined sleeping area for a first period of time, the first period of time having a duration exceeding a threshold duration associated with determining a sleeping disorder for the subject.

14. The system of claim 1, further comprising instructions executable to direct an operation of:
   posting social media status updates comprising one or more of flagged base data and flagged derivative data for presentation in an integrated social media account.

15. The system of claim 14, wherein said social media status updates are posted on behalf of the subject, with the subject being denied access to post to the account.

16. The system of claim 6, further comprising instructions executable to direct an operation of:
   posting social media status updates comprising one or more of flagged base data and flagged derivative data for presentation in an integrated social media account.

17. The system of claim 16, wherein said social media status updates are posted on behalf of the subject, with the subject being denied access to post to the account.

18. The system of claim 9, further comprising instructions executable to direct an operation of:
   posting social media status updates comprising one or more of flagged base data and flagged derivative data for presentation in an integrated social media account.

19. The system of claim 18, wherein said social media status updates are posted on behalf of the subject, with the subject being denied access to post to the account.

* * * * *